(12) United States Patent
Ikeda et al.

(10) Patent No.: US 8,237,340 B2
(45) Date of Patent: Aug. 7, 2012

(54) IGNITION PLUG AND ANALYSIS SYSTEM

(75) Inventors: Yuji Ikeda, Kobe (JP); Masashi Kaneko, Kobe (JP)

(73) Assignee: Imagineering, Inc., Kobe-shi, Hyogo (JP)

( * ) Notice: Subject to any disclaimer, the term of this patent is extended or adjusted under 35 U.S.C. 154(b) by 298 days.

(21) Appl. No.: 12/668,804

(22) PCT Filed: Jul. 12, 2008

(86) PCT No.: PCT/JP2008/062638
§ 371 (c)(1),
(2), (4) Date: Jan. 12, 2010

(87) PCT Pub. No.: WO2009/008520
PCT Pub. Date: Jan. 15, 2009

(65) Prior Publication Data
US 2010/0187968 A1    Jul. 29, 2010

(30) Foreign Application Priority Data

Jul. 12, 2007  (JP) ................................. 2007-183766

(51) Int. Cl.
*H01T 13/05* (2006.01)
(52) U.S. Cl. ...................................... 313/134; 313/118
(58) Field of Classification Search .......... 313/118–145; 123/536
See application file for complete search history.

(56) References Cited

U.S. PATENT DOCUMENTS

| 3,934,566 A | 1/1976 | Ward |
| 4,138,980 A | 2/1979 | Ward |
| 4,437,338 A * | 3/1984 | Wilson ........................ 73/114.29 |
| 2009/0229581 A1* | 9/2009 | Ikeda ............................ 123/536 |

FOREIGN PATENT DOCUMENTS

| DE | 10360193 A1 | 7/2005 |
| JP | 40-26886 Y1 | 9/1965 |
| JP | 51-77719 | 7/1976 |
| JP | 55-111086 A | 8/1980 |
| JP | 55-135162 U | 9/1980 |
| JP | 61-39881 U | 3/1986 |
| JP | 63-56557 U | 4/1988 |
| JP | 2-37486 U | 3/1990 |
| JP | 2000-274249 A | 10/2000 |

(Continued)

OTHER PUBLICATIONS

International Search Report of PCT/JP2008/062638, mailing date of Oct. 21, 2008.

*Primary Examiner* — Anne Hines
(74) *Attorney, Agent, or Firm* — Westerman, Hattori, Daniels & Adrian, LLP

(57) ABSTRACT

There is provided an ignition plug whereby an electrical configuration for discharge and an electrical configuration for guiding and radiating microwaves are provided concomitantly, within dimensions permitting installation in an installation space for an ordinary ignition plug, and adapted to efficiently guide and transmit microwaves into a combustion chamber. The ignition plug comprises a center electrode and a ground electrode for spark discharge; a center wire and an outside conductor forming a coaxial electromagnetic wave transmission line; and a microwave radiation antenna that is electrically integrated with the center wire; the microwave radiation antenna having a profile that defines part of a sphere or arc including a plurality of locations substantially equidistant from the center electrode.

20 Claims, 19 Drawing Sheets

FOREIGN PATENT DOCUMENTS

| | | |
|---|---|---|
| JP | 2001-332221 A | 11/2001 |
| JP | 2002-295259 A | 10/2002 |
| JP | 2002-295264 A | 10/2002 |
| JP | 2004-087498 A | 3/2004 |
| JP | 2005-183396 A | 7/2005 |
| JP | 2006-261941 A | 9/2006 |
| JP | 2007-032349 A | 2/2007 |
| JP | 2007-113570 A | 5/2007 |
| WO | 2008/035448 A1 | 3/2008 |

* cited by examiner

IGNITION PLUG AND ANALYSIS SYSTEM

TECHNICAL FIELD

The description relates to an ignition plug intended primarily for use in an internal combustion engine, and in particular relates to an ignition plug that is capable of spark discharge and microwave emission.

BACKGROUND OF THE INVENTION

Combusters for heat engines that utilize high frequency wave such as microwaves during ignition, such as those disclosed in Patent References 1, 2 and 3, have been proposed. However, in the combusters disclosed in these publications, the microwave antenna differs in shape and dimensions from an ordinary spark plug, and thus cannot be accommodated in the installation space for an ordinary spark plug. That is, the use of a microwave antenna requires a specialized design for the combuster, and this represents an obstacle to widespread use.

Accordingly, a system in which microwaves are guided into the combustion chamber and ignition is carried out directly with microwaves represents an attempt to address limitations relating to shape and dimensions.

The device disclosed in Patent Reference 4 is furnished internally with a coaxially disposed waveguide structure. One end of an inside conductor of the coaxial waveguide structure projects out towards the combustion chamber, while the other end constitutes the high frequency wave input end.

This input end is provided with a coupling location for an electrical energy supply line. It is possible to coaxially connect an electrical energy supply line and a center conductor to this coupling location through an inductive or capacitive coupling, thereby making it possible for electrical energy to be supplied into the waveguide structure, while achieving electrical integrity.

A system furnished with an auxiliary electrode represents another attempt to address limitations relating to shape and dimensions.

The inventors have succeeding in developing an ignition plug by drawing attention to the fact that, when a plasma is generated from air or the like, OH radicals, ozone, or other active or chemical species with high oxidative power are generated in the plasma. The ignition plug is designed to generate a plasma from a mixture of an oxidant and a fuel in the combustion chamber of a spark-ignited internal-combustion engine, in order to enhance ignition of the mixture and flame propagation subsequent to ignition, thus improving combustion of the mixture.

Furthermore, as disclosed in Patent Reference 5, the inventors were also successful in reducing the size of the ignition device mechanism employed for plasma-enhanced combustion by employing a design in which the ignition plug which is used for spark ignition and the microwave antenna which is used for plasma generation are integrated with an insulator disposed therebetween.

[Patent Reference 1] Japanese Laid-Open Patent Application 2000-274249
[Patent Reference 2] Japanese Laid-Open Patent Application 2002-295264
[Patent Reference 3] Japanese Laid-Open Patent Application 2002-295259
[Patent Reference 4] Japanese Laid-Open Patent Application 2004-087498
[Patent Reference 5] Japanese Laid-Open Patent Application 2007-113570

SUMMARY OF THE INVENTION

In the technology disclosed in Patent Reference 4, spark discharge and microwave emission cannot be attained simultaneously. Even if the device were combined with a spark plug, the complex mechanism of the coupling part formed at the input end would make it exceedingly difficult to attain the above without compromising the dimensions of a spark plug.

Another unresolved issue which relates to efficient guiding of microwaves is the inability to achieve electrical matching on the microwave transmission path leading from the microwave input end to the emission end on the combustion chamber side.

With the technique disclosed in Patent Reference 5, it is necessary to address limitations relating to dimensions etc.; to concomitantly devise an electrical configuration for spark discharge and an electrical configuration for microwave emission; and to efficiently guide and radiate microwaves into the combustion chamber.

An ignition plug and an analysis system is provided whereby an electrical configuration for discharge and an electrical configuration for guiding and radiating microwaves are both provided at a size permitting installation in an installation space for an ordinary ignition plug, and microwaves are able to be efficiently directed and transmitted into a combustion chamber.

According to a first aspect, an ignition plug comprises a center electrode and a ground electrode for spark discharge; a center wire and an outside conductor forming a coaxial electromagnetic wave transmission line; and an electromagnetic radiation antenna that is electrically integrated with the center wire; wherein the electromagnetic radiation antenna has a profile that defines part of a sphere or arc including a plurality of locations substantially equidistant from the center electrode.

According to a second aspect, an ignition plug comprises a center electrode and a ground electrode for spark discharge; a center wire and an outside conductor forming a coaxial electromagnetic wave transmission line; and an electromagnetic radiation antenna that is electrically integrated with the outside conductor; wherein the electromagnetic radiation antenna has a profile that defines part of a sphere or arc including a plurality of locations substantially equidistant from the center electrode.

According to a third aspect, the ignition plug of the first or second aspect is preferably configured to further comprises a dielectric member for covering the electromagnetic radiation antenna.

According to a fourth aspect, the ignition plug of the third aspect is preferably configured such that a basal part of the electromagnetic radiation antenna and an end of the outside conductor on the discharge gap side are embedded within the dielectric member.

According to a fifth aspect, the ignition plug of the fourth aspect is preferably configured such that a projecting portion that projects towards the discharge gap is disposed at an end on the discharge gap side of the dielectric member; and the electromagnetic radiation antenna curves along the surface of the projecting portion of the dielectric member.

According to a sixth aspect, the ignition plug of the first or second aspect is preferably configured such that the outside conductor is electrically integrated with the ground electrode, and forms a main fitting.

According to a seventh aspect, the ignition plug of the first or second aspect is preferably configured such that the insulating distance between the electromagnetic radiation antenna and the center electrode is greater than the insulating distance between the center electrode and the ground electrode; and the distance between the electromagnetic radiation antenna and any point in the space occupied by the electromagnetic radiation antenna is equal to or less than the minimum distance between the center electrode and any point on the surface of the sheath of the ignition plug.

According to an eighth aspect, an ignition plug comprises a center electrode and a ground electrode for spark discharge; a center wire and an outside conductor forming a coaxial electromagnetic wave transmission line; and an electromagnetic radiation antenna that is capacitatively coupled to the center wire; wherein the ground electrode and the outside conductor are electrically integrated; and the electromagnetic radiation antenna is grounded by the outside conductor, and has a profile that defines part of a sphere or arc including a plurality of locations substantially equidistant from the center electrode.

According to a ninth aspect, an ignition plug comprises a center electrode and a ground electrode for spark discharge; a center wire and an outside conductor forming a coaxial electromagnetic wave transmission line; and an electromagnetic radiation antenna that is capacitatively coupled to the center wire; wherein the ground electrode and the outside conductor are electrically integrated; and the electromagnetic radiation antenna is grounded by the ground electrode, and has a profile that defines part of a sphere or arc including a plurality of locations substantially equidistant from the center electrode.

According to a tenth aspect, the ignition plug of the ninth aspect is preferably configured such that the ground electrode which has been integrated with the electromagnetic radiation antenna constitutes a ring antenna.

According to an eleventh aspect, the ignition plug of the ninth aspect is preferably configured such that the ground electrode which has been integrated with the electromagnetic radiation antenna constitutes a coil antenna.

According to a twelfth aspect, the ignition plug of the eighth or ninth aspect is preferably configured such that a stub is disposed in a basal part of the electromagnetic radiation antenna.

According to a thirteenth aspect, the ignition plug of the first through twelfth aspects is preferably configured to further comprise a vane wherein one end is joined to the antenna end of the ground conductor, and the other end projects out towards the antenna.

According to a fourteenth aspect, the ignition plug of the first through thirteenth aspects is preferably configured such that the electromagnetic radiation antenna is branched at a minimum of one location.

According to a fifteenth aspect, the ignition plug of the first through fourteenth aspect is preferably configured such that the dielectric member has a plurality of members having mutually different dielectric constants.

According to a sixteenth aspect, a plasma generating equipment comprises the ignition plug of the first through fourteenth aspects; and a cap having a conductor of substantially tubular shape open at both ends wherein one opening is closed, and the inside face in the vicinity of the other opening is disposed in contact with or in a threadably mated state with the main fitting of the ignition plug about the entire circumference; wherein the insulating distance between the cap and the center electrode of the ignition plug is shortest in the vicinity of the closed opening; and the volume of a space defined by the spark plug and the cap has been selected such that a rise in pressure in the space when a plasma is generated in the space will give rise to a pressure differential equal to or greater than a prescribed value between this space and a space communicating with this space via the opening.

According to a seventeenth aspect, the plasma generating equipment of the sixteenth aspect is preferably configured such that the cap becomes progressively thinner in the vicinity of the closed opening closer towards the opening.

According to a eighteenth aspect, an analysis system is adapted to expose a specimen to a plasma so that specimen is excited, and to detect the result thereof, the analysis system, wherein a specimen is positioned in a space within a prescribed distance from the closed opening of the plasma generating equipment of the sixteenth or seventeenth aspect of the present invention, and a plasma is generated using the plasma generating equipment.

According to a nineteenth aspect, an analysis system is adapted to expose a specimen to a plasma so that the specimen is excited, and to detect the result thereof, the analysis system, wherein a plasma is generated using the ignition plug of the first through fourteenth aspects.

The ignition plug includes a center electrode and a ground electrode for spark discharge; a center wire and an outside conductor forming a coaxial electromagnetic wave transmission line; and an electromagnetic radiation antenna that is electrically integrated with the center wire; the electromagnetic radiation antenna having a profile that defines part of a sphere or arc including a plurality of locations substantially equidistant from the center electrode, whereby an electrical configuration for discharge and an electrical configuration for guiding and radiating electromagnetic waves are provided concomitantly within dimensions permitting installation in an installation space for an ordinary ignition plug, and which can efficiently guide and transmit electromagnetic waves into a combustion chamber.

Specifically, an ignition plug and an analysis system are provided whereby an electrical configuration for discharge and an electrical configuration for guiding and radiating electromagnetic waves are provided concomitantly within dimensions permitting installation in an installation space for an ordinary ignition plug, and which can efficiently guide and transmit electromagnetic waves into a combustion chamber.

DETAILED DESCRIPTION OF THE INVENTION

The preferred embodiments of the invention will be described below with reference to the drawings.

First Embodiment

Figure 1:
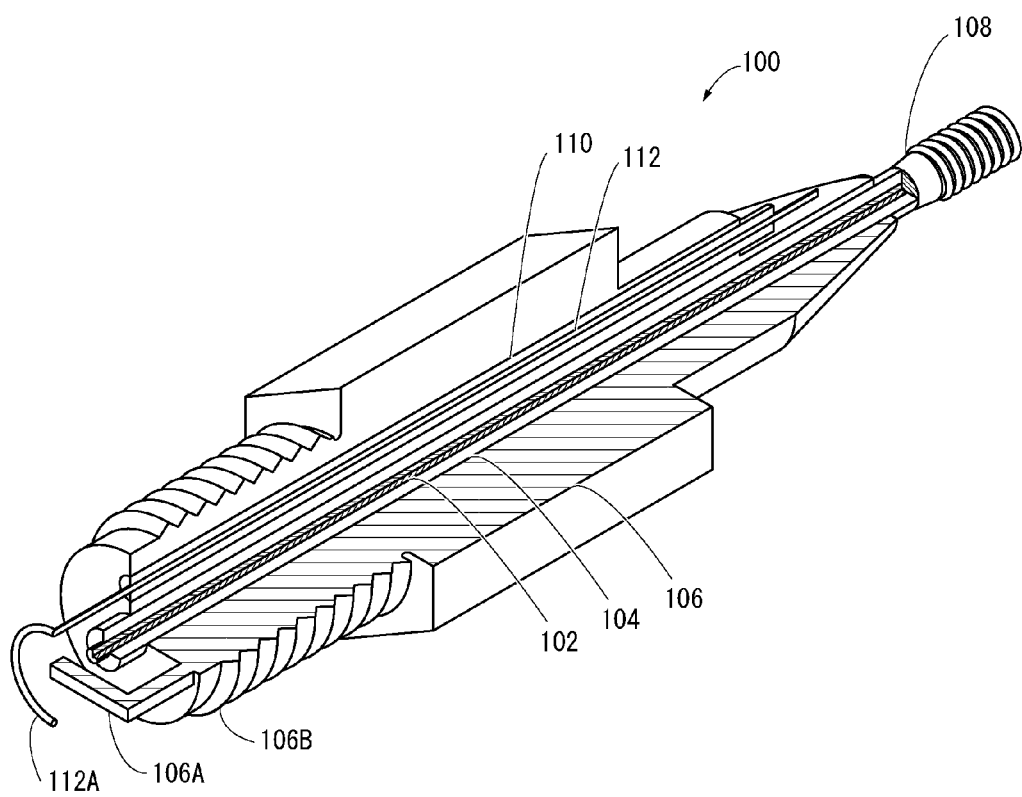
FIG. 1 is a partially cutaway perspective view of an ignition plug according to a first embodiment of the present invention.

FIG. 1 is a perspective view depicting a configuration in a first embodiment of an ignition plug according to the present invention.

As shown in FIG. 1, an ignition plug 100 according to the present embodiment has a configuration similar to an ordinary spark plug; i.e., one with a main fitting 106 having with a ground electrode, a center electrode 102, an insulator 104, and a high-voltage terminal 108; and additionally furnished with a dielectric tube 110 passing completely through the main fitting of the spark plug, and an electrical wire 112 arranged inside the dielectric tube.

The discharge gap end of the electrical wire 112 defines an antenna element 112A projecting out by prescribed length. The antenna element 112A curves (in a horseshoe shape) so as to surround the discharge gap and so as to be situated to the inward side of the thread when viewed from the discharge gap end. In this embodiment, the electrical wire 112 is made of tungsten.

The main fitting 106 functions as both the ground electrode and the outer line of a microwave transmission path. The electrical wire 112 functions as both the inner line of the microwave transmission path and an antenna. That is, the electrical wire 112, the dielectric tube 110, and the main fitting 106 constitute a coaxial microwave transmission path. Microwaves input from the high-voltage terminal 108 end are transmitted directly towards the discharge gap via the microwave transmission path. The antenna element 112A of the electrical wire 112 serves as a microwave radiation antenna. Microwaves transmitted via the microwave transmission path are radiated from this section.

In this ignition plug, a minimal number of electrical elements are needed. Consequently, compactness is easily achieved, and the transmission efficiency and radiation efficiency of microwaves may be easily improved. Additionally, both discharge and highly-efficient microwave radiation may both be achieved within the installation space for a spark plug. Microwave radiation by the antenna can be achieved over a wider effective range than with an electrode. It is therefore possible to supply microwave energy over a wider range. Additionally, due to the use of tungsten wire, a high level of heat resistance can be obtained.

Where ignition and flame propagation are enhanced by plasma using discharge and microwaves as in the technology disclosed in Patent Reference 5 mentioned above, the scale of the discharge need not be very large. It is sufficient to induce plasma (breakdown) of the mixture. Under normal circumstances, even with a very small-scale plasma having negligible development of the flame kernel, the plasma can be expanded through supply of microwave energy. The speed of plasma spread will typically be faster than the flame propagation speed. The rate of reaction of the fuel with highly active chemical species (OH radicals and ozone) produced by the expanded plasma will be faster than the rate of an ordinary combustion reaction, which is a reaction between the fuel and molecular oxygen. Through a reaction of fuel with the highly active chemical species produced by the expanded plasma, starting from the generation stage, the flame kernel will be substantially larger than the spark.

In an ordinary spark plug, the discharge gap; i.e. the distance between the center electrode 102 and the ground electrode, is made fairly wide so as to improve ignitability by application of high voltage across these electrodes. However, where plasma ignition is carried out using this ignition plug, it will be possible for reliable ignition to take place even without a wide discharge gap, and without applying higher voltage than necessary.

Second Embodiment

Figure 2:
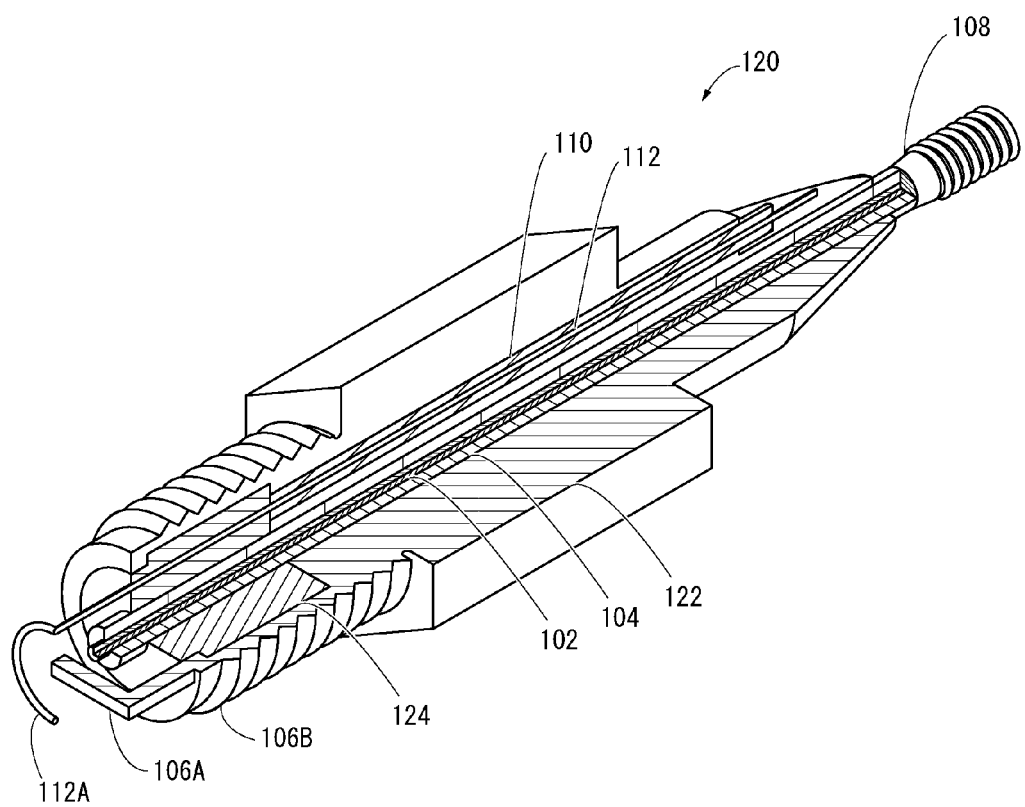
FIG. 2 is a partially cutaway perspective view of an ignition plug according to a second embodiment of the present invention.

FIG. 2 is a perspective view depicting a configuration in a second embodiment of an ignition plug according to the present invention.

The ignition plug in this embodiment is provided with a dielectric member situated at the discharge gap end. As depicted in FIG. 2, the main fitting 122 of the ignition plug 120 according to the present embodiment is furnished with a depression at the discharge gap end. A dielectric member 124 is positioned so as to fill in this depression. In this ignition plug 120, the center electrode 102, the insulator 104, and the electrical wire 112 pass completely through the main fitting 122 and the dielectric member 124.

The dielectric member 124 supports the basal part of the antenna element 112A of the electrical wire 112, as well as having the effect of extending the effective electrical length of the antenna element 112A.

In this ignition plug, the effective electrical length of the antenna element 112A section can be extended by the depression and the dielectric member 124. Thus, the gain of the antenna can be increased. Also, microwave radiation can be made more efficient. The impedance can be matched through appropriate selection of the depth and width of the depression and of the material for the dielectric member 124. This will also contribute to more efficient microwave transmission.

Modification Example 1 of Second Embodiment

Figure 3:
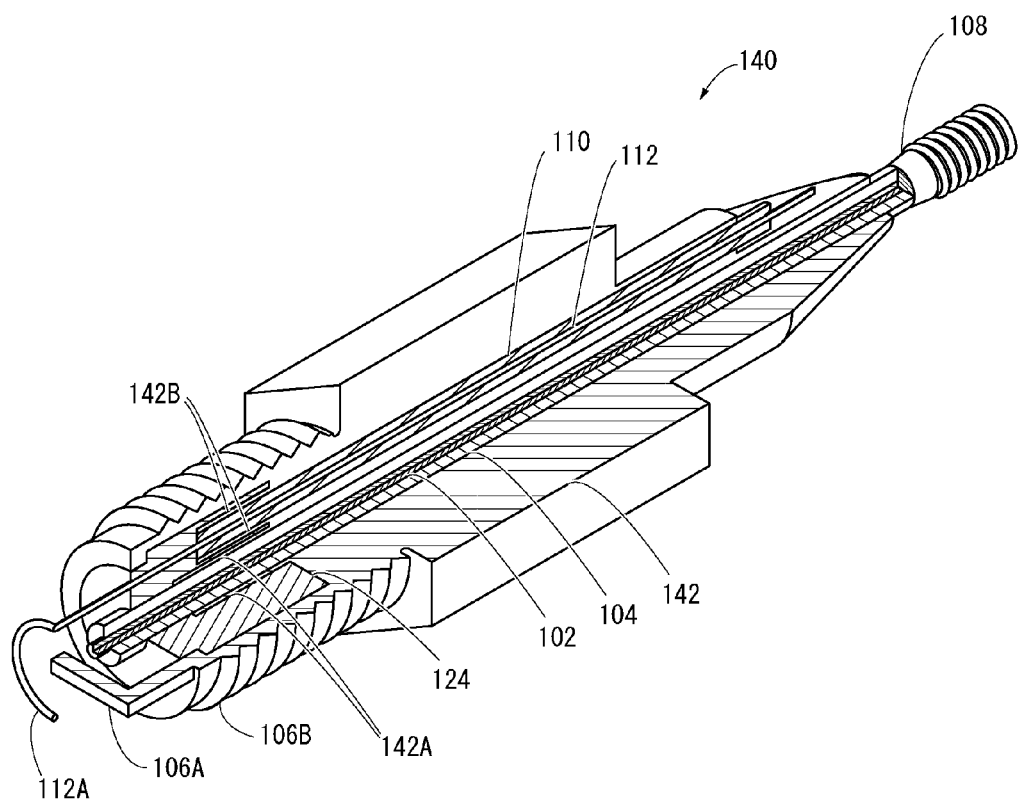
FIG. 3 is a partially cutaway perspective view of an ignition plug according to a first modification example of the second embodiment of the present invention.

As depicted in FIG. 3, in the ignition plug 140 according to Modification Example 1, the distal end of the dielectric tube 110 at the discharge gap end thereof is embedded within the dielectric member 124. The main fitting 142 of the ignition plug 140 has a section 142A that projects out with a pipe profile into the dielectric member 124 so as to encircle the side face of the insulator 104, and a projecting portion 142B that projects out with a pipe profile into the dielectric member 124 so as the encircle the side face of the dielectric tube 110.

In this ignition plug, the projecting portion 142B reflects microwaves so as to block the influx of microwave energy into the center electrode 102. The projecting portion 142B, together with the electrical wire 112 and the dielectric tube 110, define a coaxial microwave transmission path.

Energy loss is reduced by the projecting portion 142B. Counterflow of microwave energy towards the ignition signal source via the center electrode can be prevented as well. Noise is reduced thereby, and safety is improved. Additionally, it is possible to optimize impedance matching and the effective length of the antenna through proper selection of the length of the projecting portion 142B. This contributes to greater efficiency of microwave transmission.

Modification Example 2 of Second Embodiment

Figure 4:
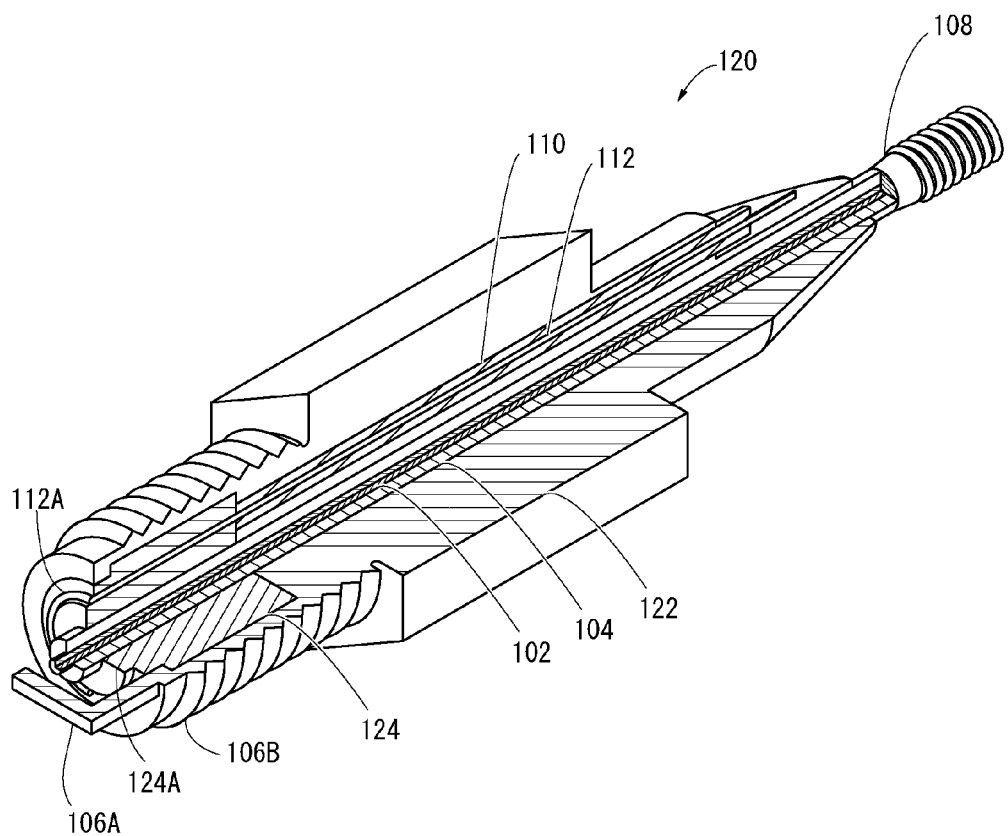
FIG. 4 is a partially cutaway perspective view of an ignition plug according to a second modification example of the second embodiment of the present invention.

As depicted in FIG. 4, in the ignition plug according to Modification Example 2, a protruding portion 124A that projects out towards the discharge gap end so as to girdle the perimeter of the insulator 104 is disposed at the discharge gap end of the dielectric member 124. At the discharge gap end of the electrical wire 112, which doubles as the antenna element, the antenna element 112A curves along the surface of the protruding portion 124A.

The protruding portion 124A functions as a mold during the bending process of the antenna. Subsequent to the bending process, the protruding portion 124A supports the antenna element 112A from its side face.

In this ignition plug, through appropriate selection of the shape of the protruding portion 124A, it is a simple matter to give the antenna element 112A the desired shape. Also, the shape will be easily retained.

In this ignition plug, by stabilizing the antenna element 112A in the desired shape, it is possible to obtain good microwave radiation characteristics.

Modification Example 3 of Second Embodiment

Figure 5:
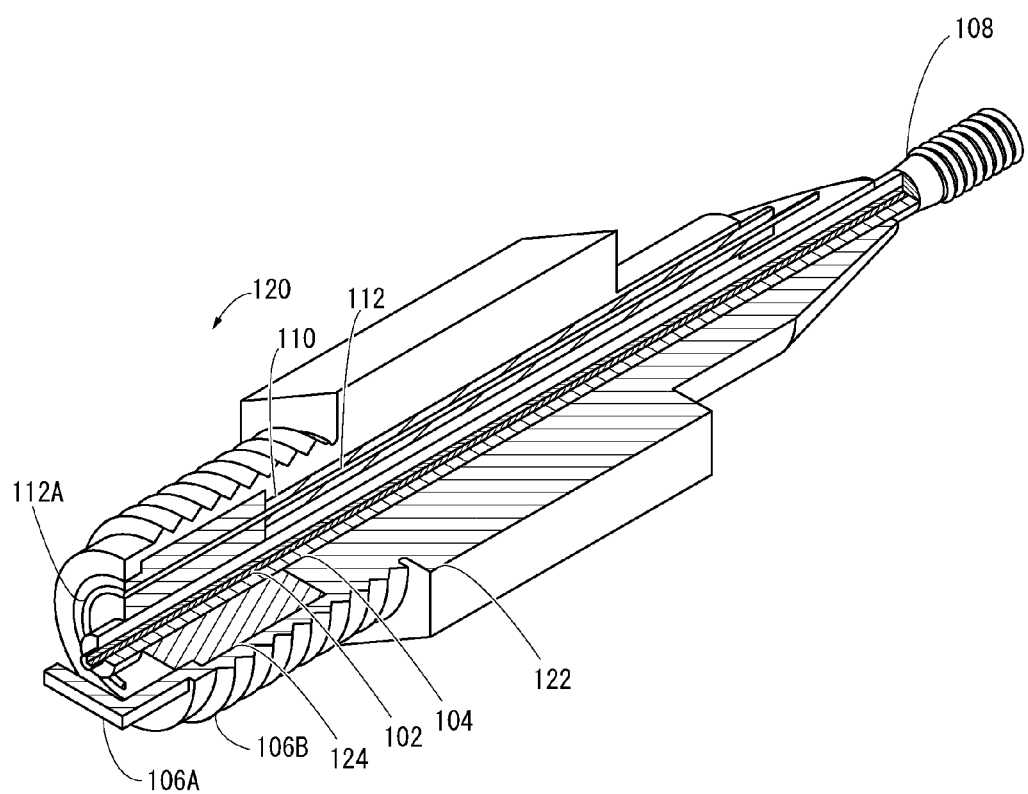
FIG. 5 is a partially cutaway perspective view of an ignition plug according to a third modification example of the second embodiment of the present invention.

As depicted in FIG. 5, the ignition plug according to the present modification example has been designed with the antenna element 112A embedded halfway into the dielectric element 124.

In this ignition plug, because the antenna element 112A is supported by the dielectric element 124, mechanical strength is improved.

Modification Example 4 of Second Embodiment

Figure 6:
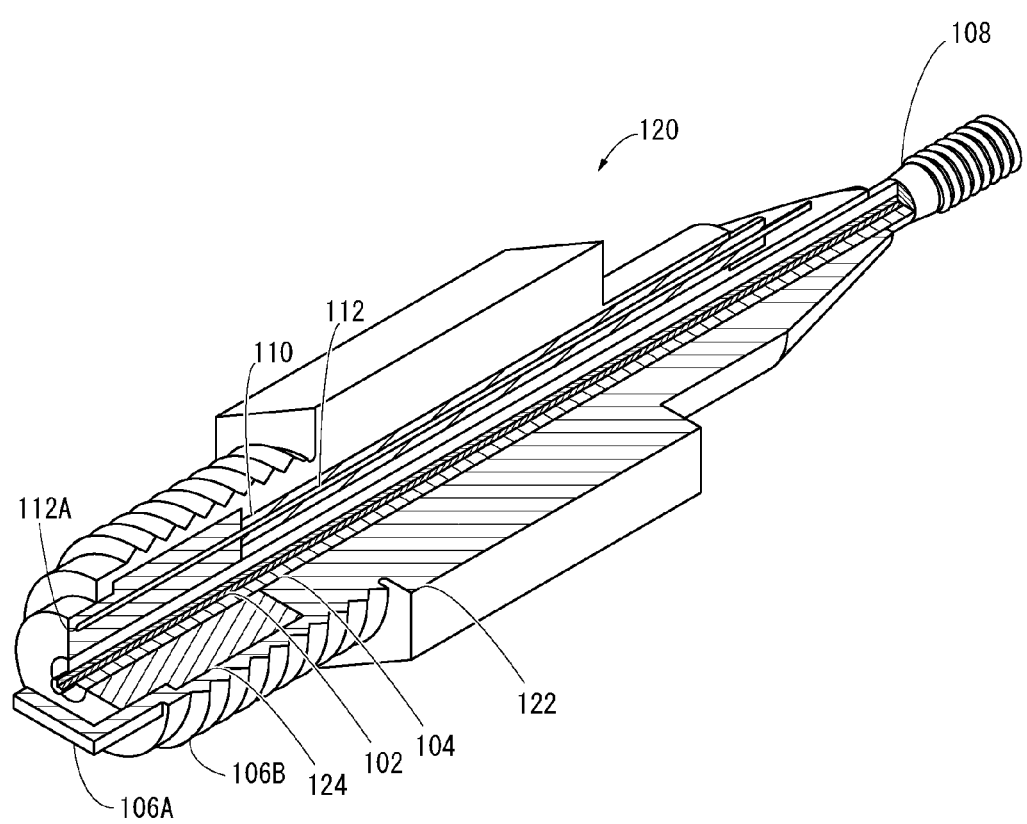
FIG. 6 is a partially cutaway perspective view of an ignition plug according to a fourth modification example of the second embodiment of the present invention.

As depicted in FIG. 6, the ignition plug according to the present modification example has been designed with the antenna element 112A embedded completely within the dielectric element 124.

Since the antenna element 112A is supported by the dielectric element 124, the mechanical strength of the ignition plug is improved.

Modification Example 5 of Second Embodiment

Figure 7:
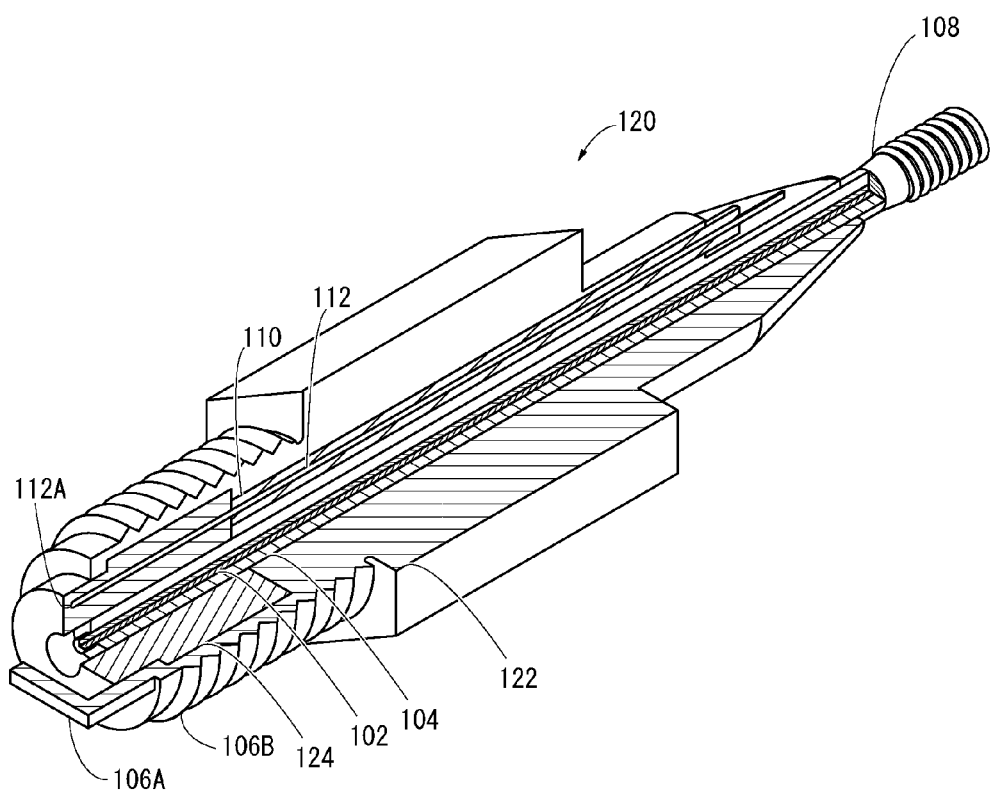
FIG. 7 is a partially cutaway perspective view of an ignition plug according to a fifth modification example of the second embodiment of the present invention.

As depicted in FIG. 7, the ignition plug 120 according to the present modification example has been designed with the antenna element 112A embedded completely within the dielectric element 124. Where this is to be used for plasma ignition, it is acceptable for the distal end of the center electrode 102 on the discharge gap end thereof to be situated on the high-voltage terminal 108 side of the end face of the dielectric member 124 at the discharge gap end thereof.

According to the ignition plug, the action of the microwaves on the discharge spark produced in the gap can take place more effectively, while the mechanical strength is improved.

Some of the antenna element 112A may be exposed to the exterior.

Modification Example 6 of Second Embodiment

Figure 8:
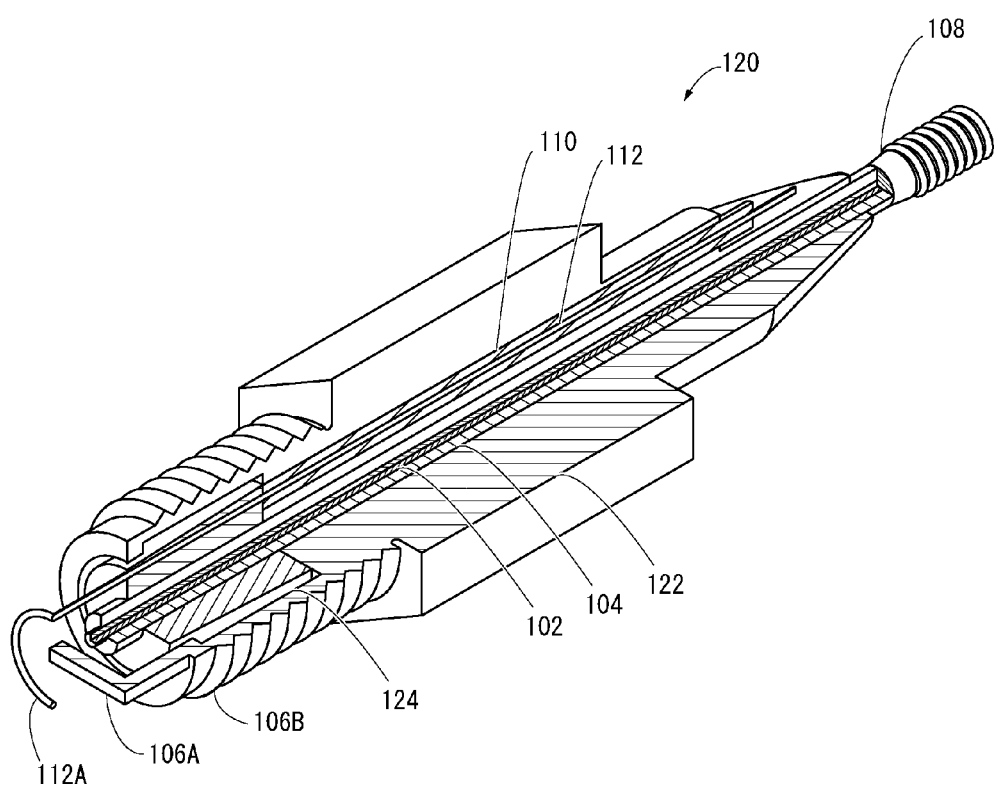
FIG. 8 is a partially cutaway perspective view of an ignition plug according to a sixth modification example of the second embodiment of the present invention.

As depicted in FIG. 8, the ignition plug 120 may also be furnished with a gap between the main fitting 122 and the dielectric member 124. The insulating distance of the antenna element 112A and the main fitting 122 can be adjusted through this gap.

Third Embodiment

Figure 9:
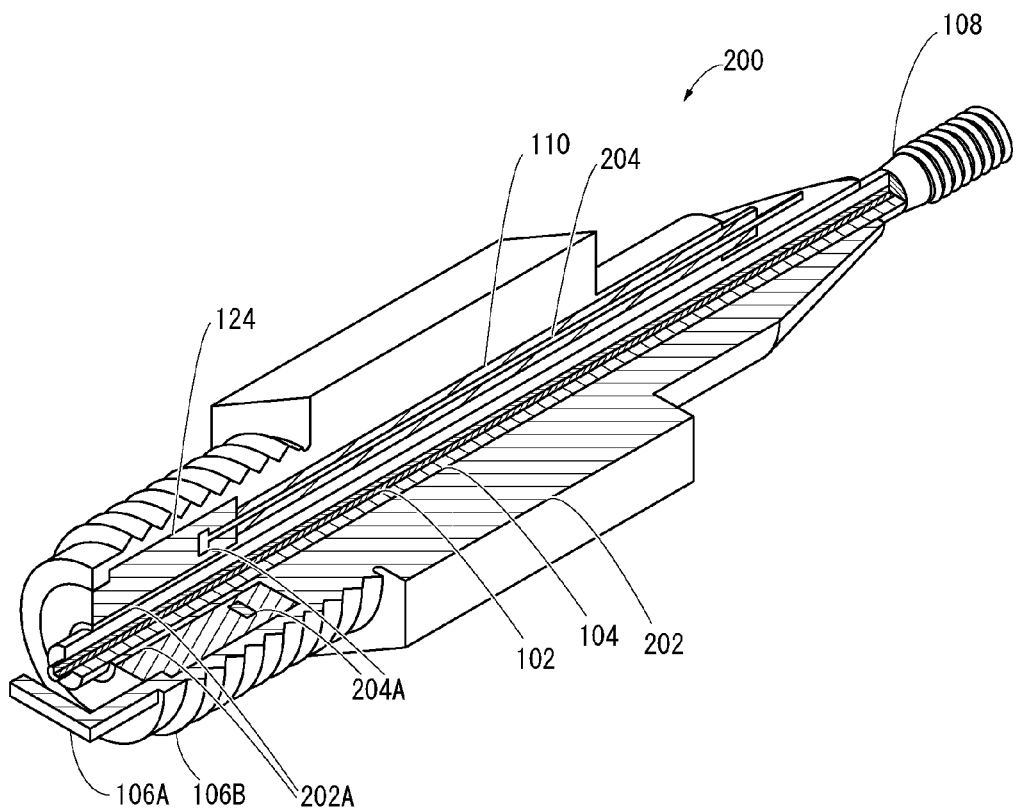
FIG. 9 is a partially cutaway perspective view of an ignition plug according to a third embodiment of the present invention.

The ignition plug in this embodiment has been designed with the antenna buried at a deeper location in the interior than the plug end face. As depicted in FIG. 9, in this ignition plug 200, a microwave shield 202A of tubular form passing through the dielectric member 124 so as to encircle the insulator 104 has been provided in the main fitting 202. The end of the electrical wire 204 at the discharge gap end thereof has been embedded within the dielectric member 124, and a coupling ring 204A of annular form that surrounds and maintains a prescribed distance from a pipe antenna is provided in this section.

In this ignition plug, microwaves radiated from the antenna element 204A of the electrical wire 204 are capacitatively coupled to a resonant cavity that is constituted by the microwave shield 202A and the main fitting 202.

The microwave shield 202A projects out beyond the body of the main fitting 202. Thus, the section surrounding the dielectric member 124 inclusive of the microwave shield 202A defines a resonant space. Microwaves that resonate inside the resonant space are radiated towards the discharge gap. As a result, electrical field intensity on the spark gap side will be elevated by the microwaves.

In this ignition plug, through capacitive coupling in the antenna/transmission path coupling section where impedance matching is most needed, impedance matching can be accomplished while ensuring transmission efficiency of microwaves within the plug. Microwave radiation efficiency will be improved thereby. Also, the microwave transmission section has a simple construction, and space sufficient to ensure transmission efficiency can be assured.

Modification Example of Third Embodiment

Figure 10:
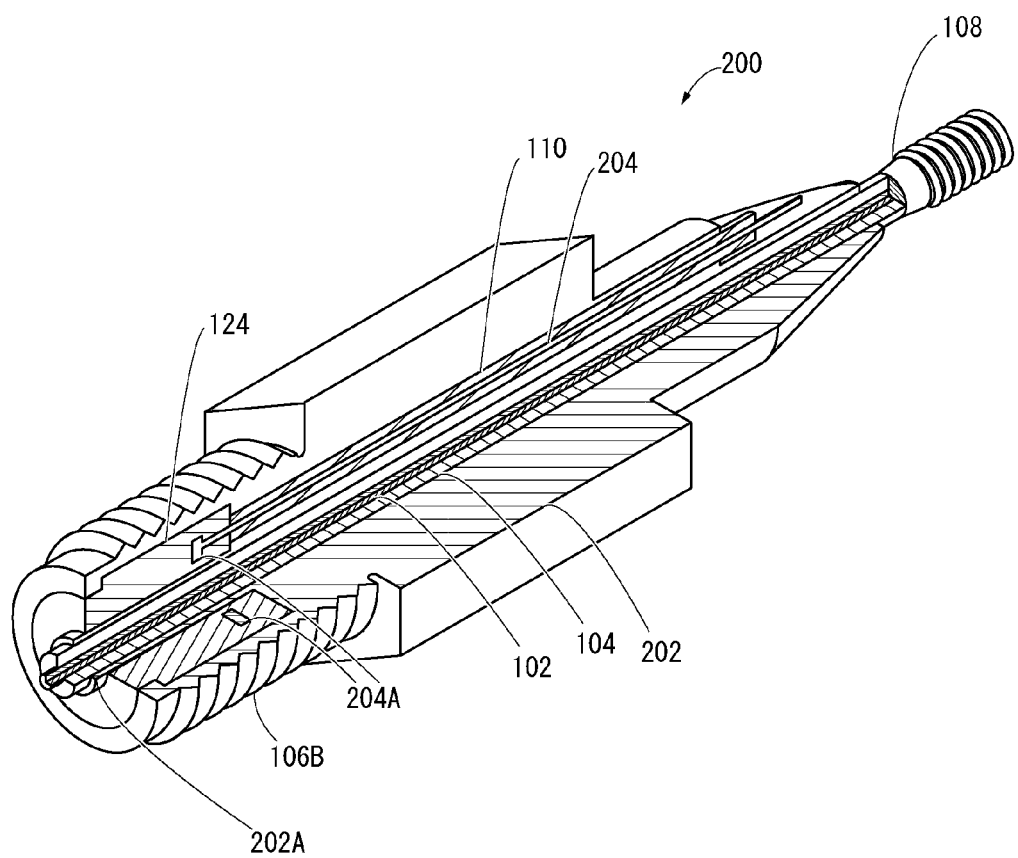
FIG. 10 is a partially cutaway perspective view of an ignition plug according to a modification example of the third embodiment of the present invention.

As depicted in FIG. 10, in the ignition plug 200 in this modification example, the microwave shield 202A doubles as the ground electrode. In this instance, discharge will occur along the surface of the insulator 104. In this configuration, the microwave shield 202A may project outward by a prescribed length from the dielectric member 124.

Fourth Embodiment

Figure 11:
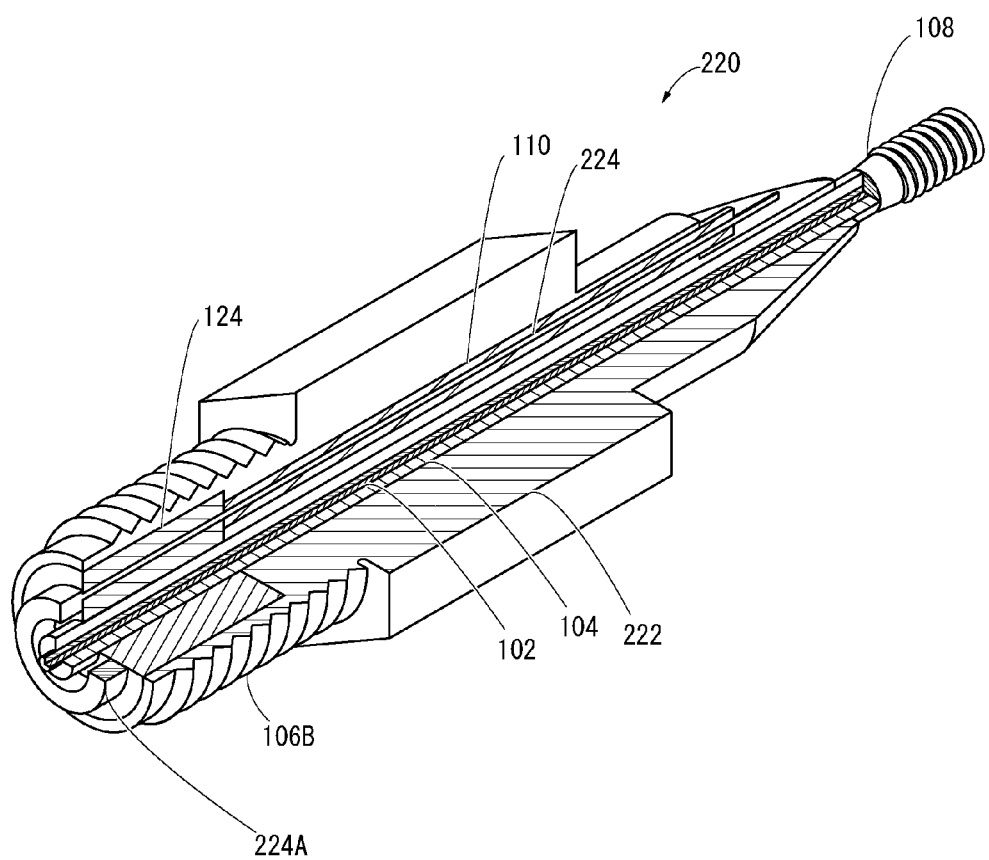
FIG. 11 is a partially cutaway perspective view of an ignition plug according to a fourth embodiment of the present invention.

In the ignition plug of this embodiment, the electrical wire doubles as the antenna and as the ground electrode. As shown in FIG. 11, this ignition plug 220 is furnished with a center electrode 102, an insulator 104, a high-voltage terminal 108, a dielectric member 124, a dielectric tube 110, a main fitting 222, and an electrical wire 224 that passes through the dielectric tube 110 and the dielectric member 124.

To the opposite end of the electrical wire 224 from the high-voltage terminal 108 there is provided a ring portion 224A that lies exposed so as to encircle the exposed sections of the center electrode 102 and the insulator 104. During use of the ignition plug 220, the electrical wire 224 will receive application of microwave signals, and will be grounded via a stub having prescribed electrical length.

Once the electrical wire 224 is grounded via the stub, it will function as a grounded conductor with respect to direct current, but will function as an ungrounded conductor with respect to microwaves. In the ignition plug 220, the main fitting 222 lacks the function of the ground electrode. Instead, the high-voltage electrical wire 224 is provided with the function of the ground electrode. That is, the electrical wire 224 serves as the center line of the microwave transmission path, as the microwave radiation antenna, and also as the ground electrode.

When a high-voltage ignition signal is applied to the center electrode 102, discharge will occur between the center electrode 102 and the ring portion 224A. At this time, electrical current will travel to the contact point via the center electrode 102, the electrical wire 224, and the stub. Counterflow of unmodified electrical current to the microwave signal source does not take place.

When a microwave signal is applied to the electrical wire 224, microwaves will be transmitted to the ring portion 224A via a microwave transmission path composed of the main fitting 222, the dielectric tube 110, and the electrical wire 224. Microwaves will then be radiated from the ring portion 224A.

In this ignition plug 220, induced loss to the key-shaped ground electrode will not occur. Microwave radiation can thus take place more efficiently. Also, owing to the construction, microwave energy can readily be concentrated in the spark section.

Modification Example 1 of Fourth Embodiment

Figure 12:
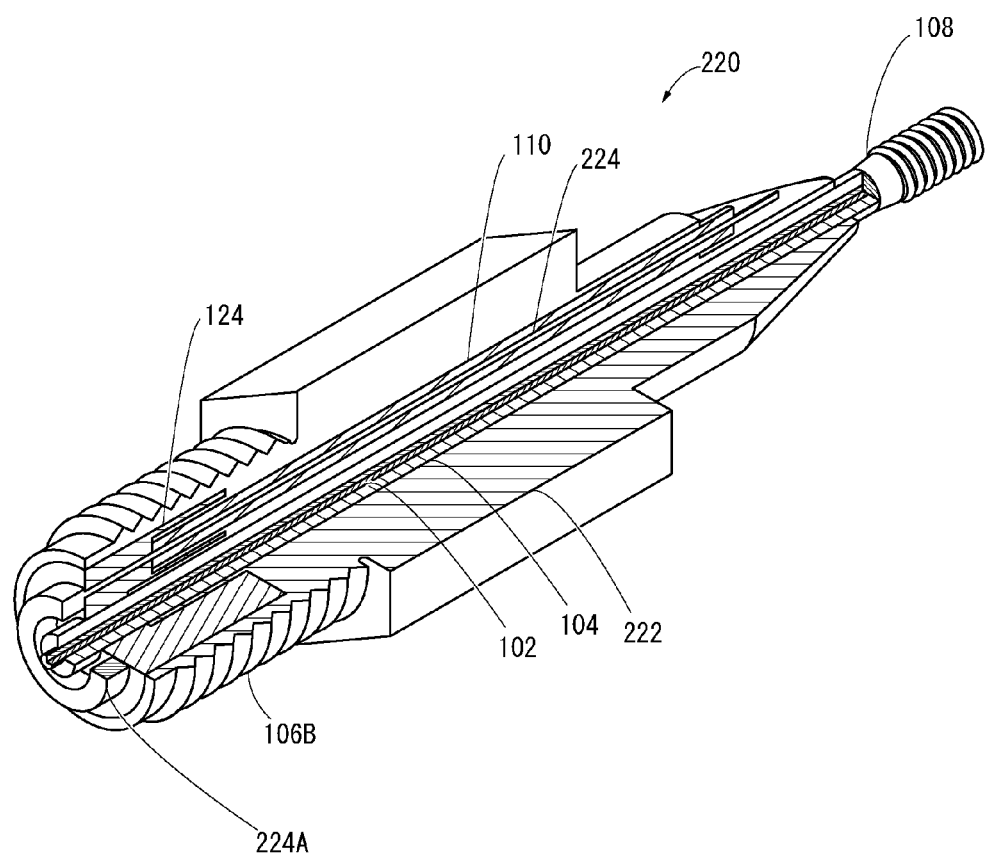
FIG. 12 is a partially cutaway perspective view of an ignition plug according to a first modification example of the fourth embodiment of the present invention.

As depicted in FIG. 12, in this ignition plug, part of the boundaries of the dielectric member 124, the insulator 104, and the dielectric tube 110 may be sheathed by the main fitting 106 as in Modification Example 1 of the Second Embodiment. By so doing, the working effects of Modification Example 1 of the Second Embodiment may be attained in the ignition plug of the Fourth Embodiment.

Modification Example 2 of Fourth Embodiment

Figure 13:
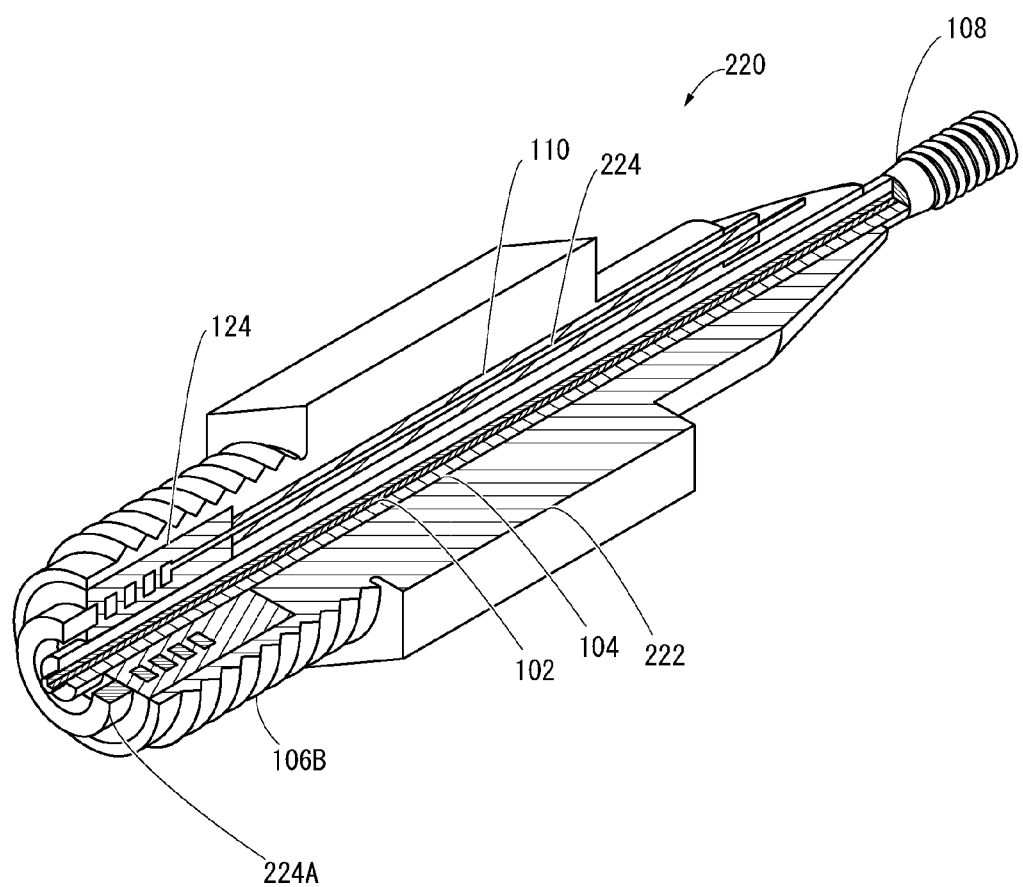
FIG. 13 is a partially cutaway perspective view of an ignition plug according to a second modification example of the fourth embodiment of the present invention.

As depicted in FIG. 13, in this ignition plug, a coil may be formed in the section where electrical wire 224 is embedded in the dielectric member 124. Inductance similar to a coil antenna can thus be obtained at the distal end of the electrical wire 224. Impedance matching can be achieved through selection of the shape of the coil section.

Modification Example 3 of Fourth Embodiment

Figure 14:
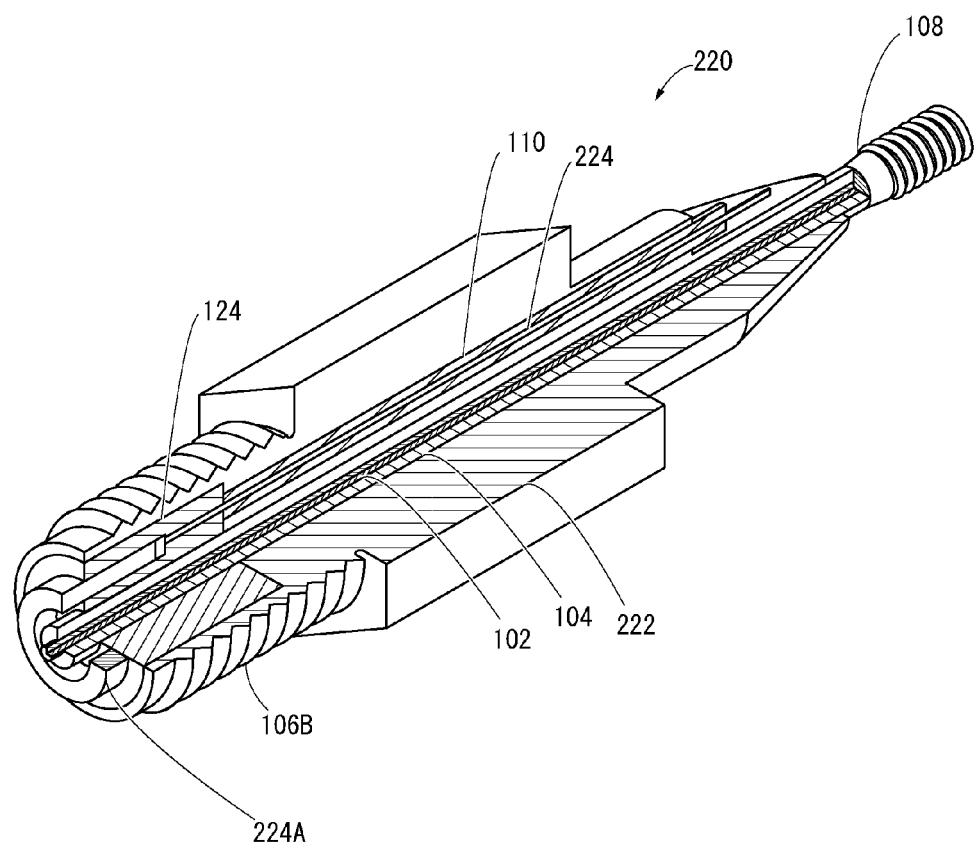
FIG. 14 is a partially cutaway perspective view of an ignition plug according to a second modification example of the fourth embodiment of the present invention.
Figure 15:
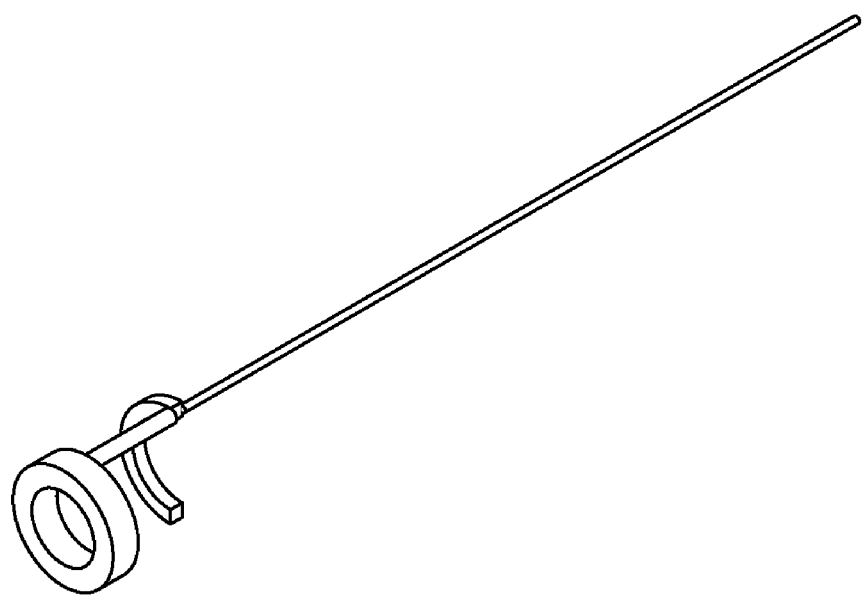
FIG. 15 is a perspective view of the antenna of an ignition plug according to a modification example of the fourth embodiment of the present invention.

FIG. 14 depicts the ignition plug of the present modification example, and FIG. 15 depicts electrical wire and antenna shape in this ignition plug.

As shown in FIGS. 14 and 15, in this ignition plug, a stub may be provided in the section where electrical wire 224 is embedded in the dielectric member 124. Through selection of the length of the stub section, impedance matching can be achieved and microwave radiation efficiency can be enhanced.

Alternative Modification Examples

Figure 16:
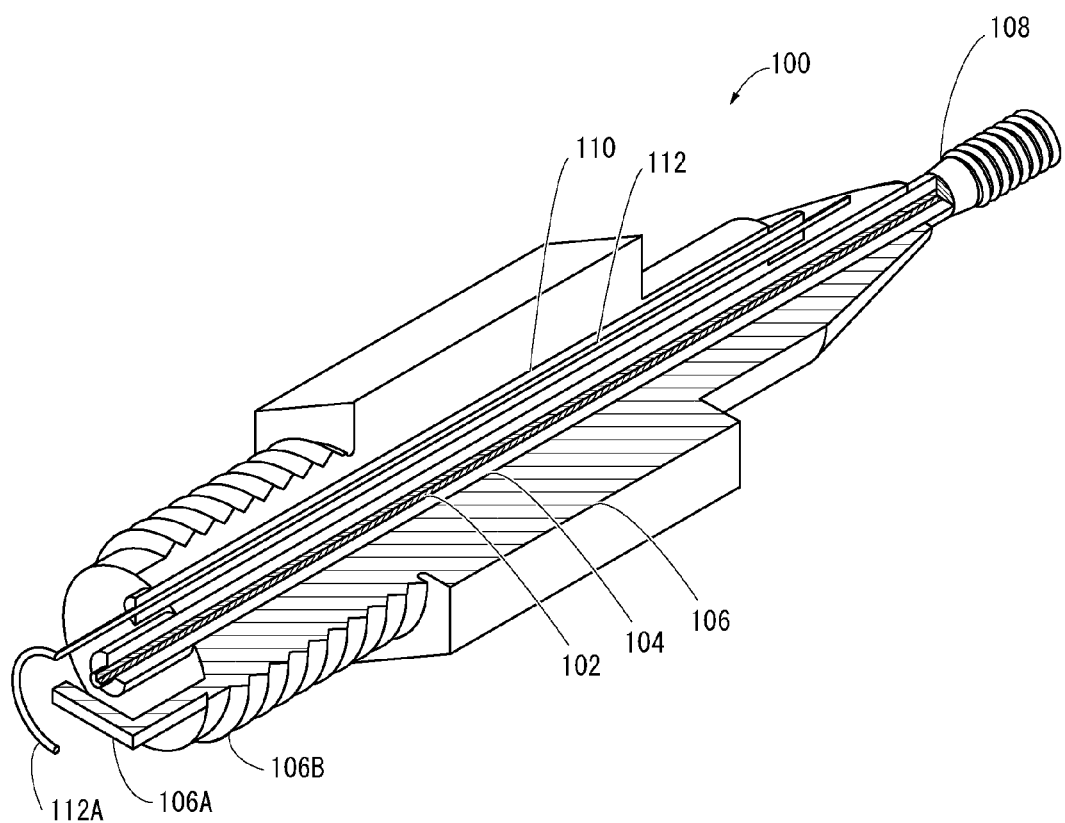
FIG. 16 is a partially cutaway perspective view of an ignition plug according to the present invention, having a faceted reflecting surface.

In the ignition plug 100 according to the present invention, the face of the main fitting situated in opposition to the radiating end of the antenna may be given a curving face as depicted in FIG. 16. For example, by adopting a paraboloidal surface having the radiating end as its focal point, directionality in one direction will be higher. Alternatively, by adopting an elliptical surface and designing the radiating end to be one focal point of the elliptical surface, reflected waves at this surface will concentrate at the other focal point.

By utilizing such reflection by the main fitting, it will be possible to attain desired directionality.

Of the several embodiments discussed above, for those in which the ground electrode 106A projects out, the ground electrode section may be given a curving surface structure in order to achieve directionality.

With regard to the shape of the section constituting the antenna element, a shape that produces directionality in the microwave radiation characteristics may be selected as well. By imparting directionality to microwave radiation characteristics in this way, microwave energy can be concentrated in a desired area or direction.

Additionally, whereas in the preceding embodiments the main fitting was described as being an integral member, it may instead be formed by a plurality of members. Also, the insulator and the dielectric member may be formed using an integral member.

The material of the antenna is not limited to tungsten. For designs in which the antenna is exposed, inconel or nickel alloys are also acceptable. Where the antenna is exposed, a coating of iridium, gold, platinum, silver or the like may be provided to enhance corrosion resistance.

The ground electrode may be comparable to one in an ordinary spark plug. For example, a plurality of ground electrodes could be provided, as in a so-called multipole plug. Also, the sheath (screw portion) of the main fitting could serve as the ground electrode, as in racing spark plugs and creeping discharge type spark plugs.

Modification Example with Added Vanes

The ignition plugs according to the preceding embodiments may be additionally designed with vanes projecting out from the main fitting. An example of a plug furnished with such vanes is depicted in FIG. 17.

Figure 17:
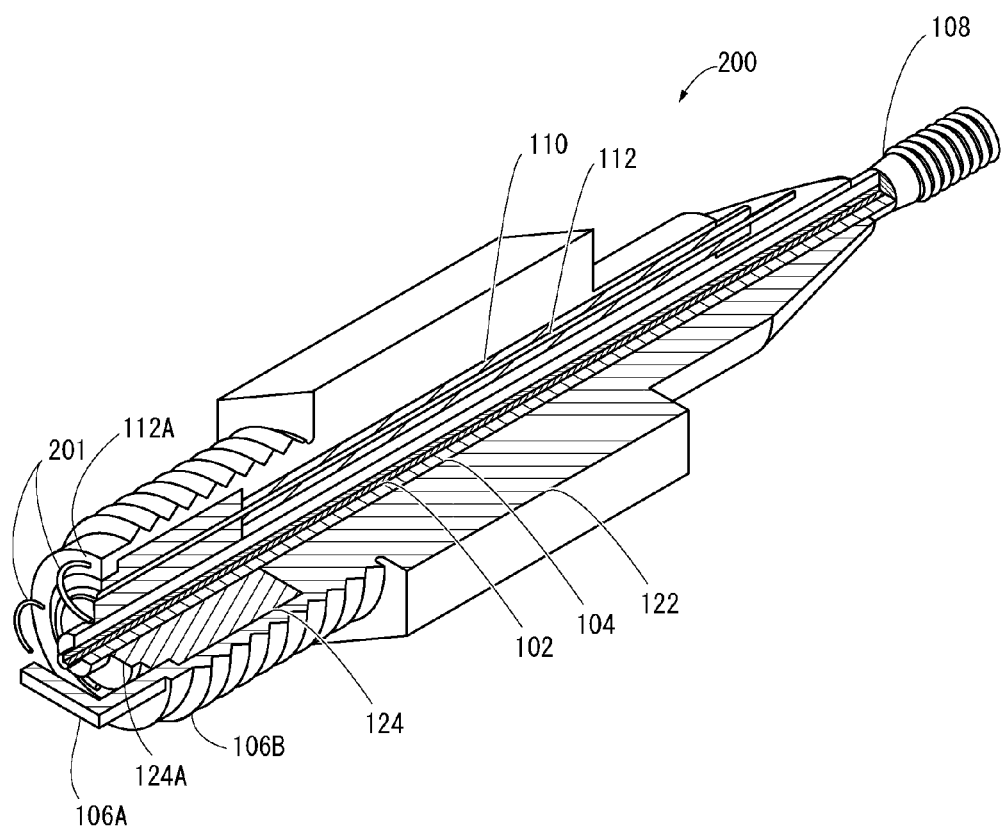
FIG. 17 depicts an example of a plug furnished with vanes.

The ignition plug 200 depicted in FIG. 17 is furnished with an internal construction comparable to that of the ignition plug depicted in FIG. 4. This ignition plug 200 is further provided with vanes 201 composed of conductors and projecting out towards the antenna from the distal end (i.e. the end where antenna is situated) of the main fitting 106. In preferred practice the length of the vanes will be close to one-fourth the wavelength of the electromagnetic waves radiated by the antenna 112A while remaining within the permissible range imposed by dimensional limitations, but is not necessarily limited to one-fourth.

The vanes 201 are situated close to the antenna 112A at the distal end. When discharge occurs between the center electrode 102 and the ground electrode 106A, and electromagnetic waves are radiated by the antenna 112A, a portion of the energy of the electromagnetic waves is used in expansion of the plasma which has been generated by discharge, while another portion forms a strong electric field between the antenna 112A and the vanes 201. As charged particles (electrons, ions etc.) derived from the expanded plasma reach the area of this strong electric field, the charged particles will receive energy in the area of the strong electric field, generating a plasma in this area. As a result, plasma will occur not just in proximity to the center electrode 102, but in proximity to the vanes 201 as well. That is, plasma will occur prominently at multiple sites.

While in this modification there is shown an example wherein vanes have been added to the ignition plug depicted in FIG. 4, vanes may be added to any of the ignition plugs according to the embodiments described above. Also, the vanes 201 and the antenna 112 may constitute a so-called ESPAR antenna.

Additional Modification Examples of Ignition Plug

In the preceding embodiments, ignition plugs resembling spark plugs in shape have been shown by way of example, but the ignition plug according to the present invention is not limited thereto. For example, a shape resembling a glow plug furnished with discharge electrodes, a microwave transmission path, and an antenna would be acceptable as well. Such an ignition plug could additionally be furnished with heating means such as a filament or a ceramic heater. One of the conductor pair which make up the discharge electrodes may be the glow plug filament, or a conductor connected to the glow plug filament.

In the present invention, the energy for discharge may be AC, and the frequency thereof may be a high frequency wave. An electrical signal of superimposed DC electricity and AC or high frequency wave is also acceptable. Of the energy applied to the center electrode, the AC or high frequency wave component need not only give rise to discharge, and may be radiated as electromagnetic waves from the center electrode as well. Further, an area of a strong electric field may be produced through superimposition of electromagnetic waves radiated from the electromagnetic radiation antenna and electromagnetic waves radiated from the center electrode.

In the ignition plug according to the present invention, the thickness of the electromagnetic radiation antenna may be uniform, or alternatively, thickness may vary in each region. Impedance of the antenna can be adjusted through adjustment of thickness, making it possible to boost the electromagnetic wave radiation efficiency.

The electromagnetic radiation antenna may be one composed of a single material, or one composed of a combination of components made of several materials. When combining components made of several materials, component selection will preferably be carried out in view of the electromagnetic radiation antenna and plasma formation location. For parts which will be exposed to plasma, materials that experience minimal wear damage with exposure to heat or plasma may be selected. For parts that will receive transmission of electromagnetic waves, highly conductive materials may be selected.

For sections coupled with an insulator or conductor, selection of a material having a thermal expansion coefficient approximating that of the insulator or conductor can reduce heat-induced strain or breakage.

In the ignition plug according to the present invention, it is not essential that the electromagnetic radiation antenna be of single element type. A so-called multielement antenna with branched elements is also acceptable. The branched elements may be arranged to produce counterpoise; alternatively, the elements may extend in a prescribed direction, or radially.

Phase differences may be introduced into the electromagnetic waves that are radiated by the several branched elements, in order to orient the electromagnetic wave radiation direction towards a particular location or direction. It is not essential for the branched elements to be in constant electrical unification with one another. For example, utilizing thermal expansion of the elements, the elements may be designed to contact one another only when a prescribed temperature condition has been met. By so doing, the element configuration used to generate electromagnetic waves can be selected according to temperature conditions.

In the ignition plug according to the present invention, components made of several materials may be combined to constitute the components composed of conductors. For example, concentration of electromagnetic wave energy can be promoted by creating a lens effect. Alternatively, by combining components that differ in dielectric constant, and reflecting the electromagnetic waves at their interfaces, leakage of electromagnetic waves can be reduced.

Additionally, various components can be combined in various desired combinations so as to obtain a desired electric field or distribution thereof. For some of the components composed of conductors, materials having high responsiveness to temperature changes produced by inductive heating with microwaves can be selected. By so doing, this ignition plug can adjust the temperature of the conductor components through radiation of electromagnetic waves.

In some instances the dielectric constant of a conductor varies according to temperature. By adjusting or controlling temperature, the desired dielectric constant can be obtained, and it will also be possible to regulate electromagnetic wave transmission efficiency and radiation efficiency.

Fifth Embodiment

Figure 18:
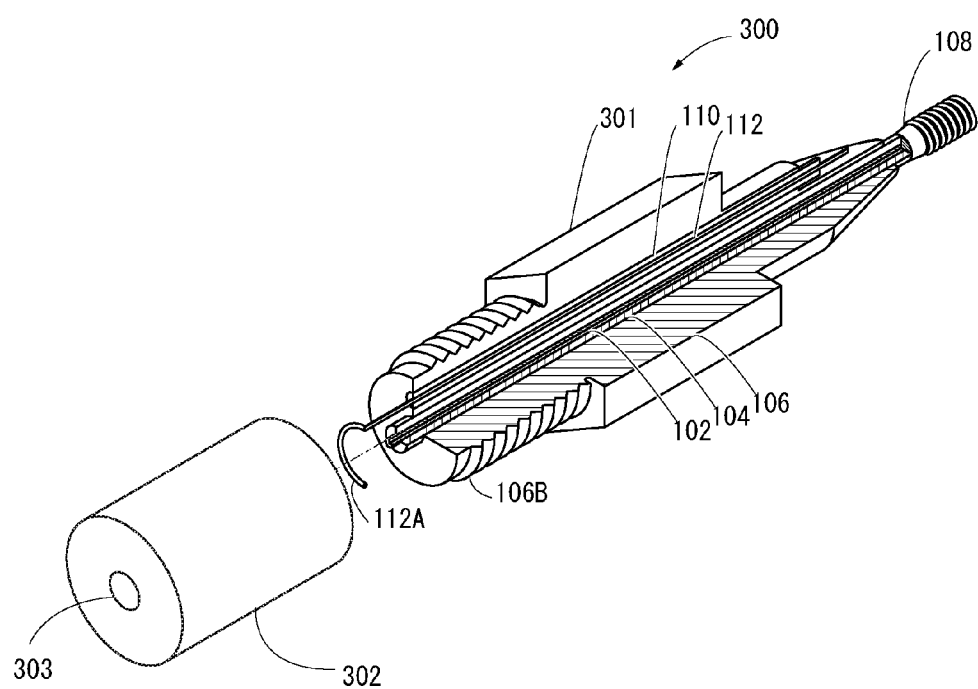
FIG. 18 depicts a configuration of a plasma-generating unit employing the ignition plug according to the present invention.

FIG. 18 depicts a configuration of a plasma generating equipment 300 which employs the ignition plug according to the embodiments described above.

This plasma generating equipment 300 is furnished with an ignition plug 301 whose internal construction is comparable to that of the ignition plug 100 according to the First Embodiment depicted in FIG. 1; and a cap 302 made of a conductor and threadably mated with the plug body section of the main fitting 106A of the ignition plug 301 so as to surround the distal end of the ignition plug 301. In this ignition plug 301, the ground electrode 106A of the ignition plug 100 according to the first embodiment has been cut off.

The cap 302 has a tubular shape that is closed at the opposite end from its threadable mating portion, and the spaces inside and outside the cap communicate through an opening 303 at the closed end. The cap 302 has its minimum insulating distance in the vicinity of the center electrode of the ignition plug 301 and the opening 303. In the vicinity of the opening 303 of the cap 302 the member has been molded so as to be progressively thinner closer to the opening 303.

When the ignition plug 100 receives an ignition signal, discharge will occur in the vicinity of the opening 303 inside the cap 302. Under this condition, when the ignition plug 100 receives a feed of electromagnetic waves, electromagnetic waves will be radiated from the antenna 112A, forming a strong electric field in the vicinity of the opening 303. The result will be expansion of the plasma which has been generated through discharge in an area in the vicinity of the opening 303 inside the cap 302. This plasma will produce heating of gases inside the empty cap 302, causing pressure inside the cap 302 to rise. This will in turn give rise to a pressure differential between the cap 302 interior and the outside. The plasma generated in the vicinity of the opening 303 will be pushed to the outside due to this pressure differential. As a result, the plasma will be sprayed out from the section of the opening 303.

Because the plasma generating equipment 300 has a construction whereby plasma is sprayed out utilizing a pressure differential, the volume of the space that is defined by the ignition plug 301 and the cap 302 will be selected so as to achieve a pressure differential sufficient for the plasma to be sprayed out due to a pressure rise taking place in association with heating of the plasma. The pressure differential sufficient to bring about spray of plasma will be determined by the physical properties; e.g. the viscosity, of the generated plasma and by the input energy to the ignition plug 301. Accordingly, an appropriate volume of this space will be determined with reference to input energy and the source gases of the plasma.

According to the present embodiment, spraying of plasma can be accomplished with a simple construction involving covering the ignition plug 301 with a cap 302. By selecting a construction whereby the ignition plug 301 and the cap 302 threadably mate, it is a simple matter to adjust the volume of the space in which the plasma is generated. Moreover, by molding the cap 302 so that it is thinner in the vicinity of the opening 303, coupling between the component in the vicinity of the opening 303 and the antenna 112A will be enhanced, and it will be easier to obtain a strong electric field in the vicinity of the opening 303.

In the present embodiment, the cap 302 is composed of a conductor, but it is not necessary for the cap 302 to be entirely composed of a conductor. Provided that there is a conductor section extending at a minimum from the proximity of the opening 303 to the section contacting the main fitting 106, other sections of the cap 302 need not be composed of a conductor. For example, the inside face of a cap made of ceramic may be coated with a metal layer. However, in order to prevent electromagnetic wave leakage and enhance electric field strength inside the cap 302, it is preferable at a minimum for the entire inside face of the cap 302 to be a conducting face.

In the present embodiment, the ignition plug 300 has a construction equivalent to the ignition plug 100 shown in FIG. 1, but a construction equivalent to the ignition plug according to any of the other embodiments and modification examples is acceptable as well.

The vicinity of the opening 303 of the cap 302 may be forcibly cooled using a water-cooled or air-cooled system, or the like. This can reduce wear damage caused by heat in the vicinity of the opening 303. It can also lower the gas temperature. This will contribute to thermal nonequilibrium of the sprayed plasma.

Sixth Embodiment

With the ignition plug 300 according to the Fifth Embodiment, it is possible to spray plasma with a compact and simple construction. This plasma may be employed for ignition of an internal-combustion engine or the like, or as a plasma source for use in componental analysis. In the present embodiment, an analysis system employing plasma is shown as an example of application as a plasma source.

Figure 19:
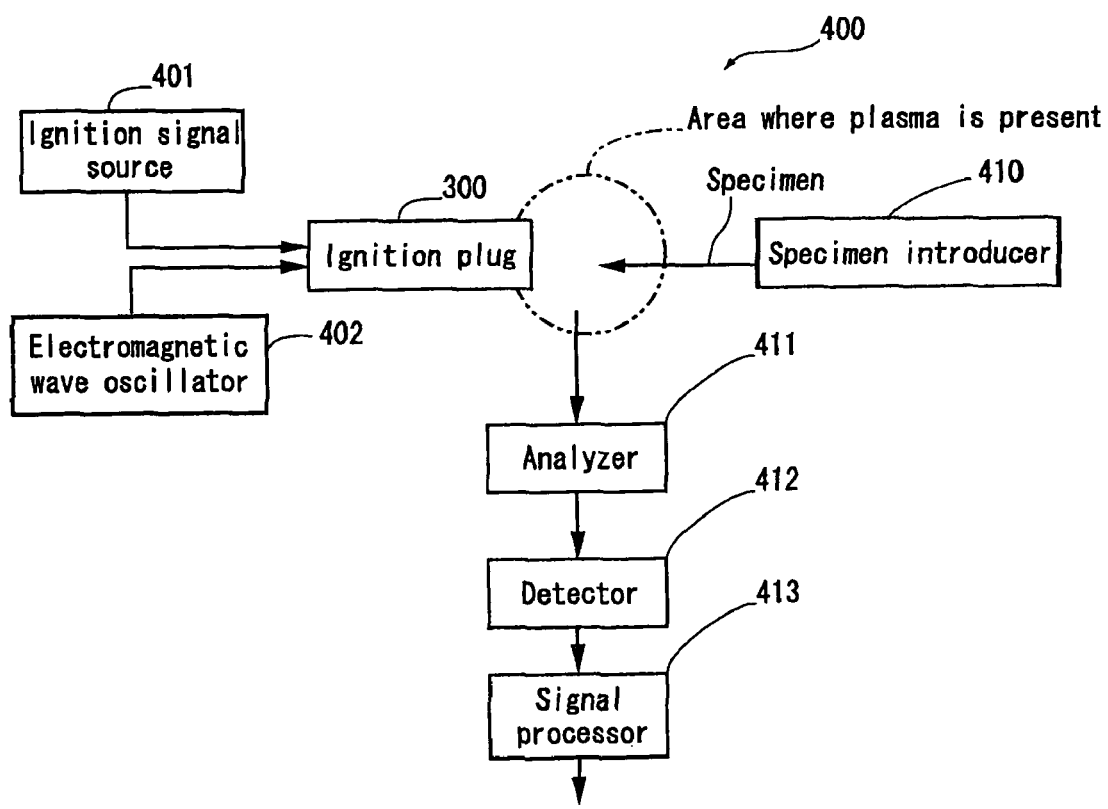
FIG. 19 depicts a simplified configuration of the analysis system according to the embodiment.

FIG. 19 is a drawing depicting a simplified configuration of the analysis system according to the present embodiment.

The analysis system 400 shown in FIG. 19 includes the ignition plug 300 according to the Fifth Embodiment; an ignition signal source 401 adapted to apply DC pulse voltage for discharge of the ignition plug 300; an electromagnetic wave oscillator 402 adapted to feed electromagnetic waves to the ignition plug 300; a specimen introducer 410 adapted to introduce and position a sample in an area where a plasma sprayed from the ignition plug 300 is present; an analyzer 411 for carrying out analysis of the results obtained when the specimen is exposed to the plasma from the ignition plug 300; a detector 412 adapted to convert the results analyzed by the analyzer 411 into a signal of prescribed format; and a signal processor 413 adapted to carry out processing of the signal from the detector 412, and present the detection and analysis results to the user.

The specimen introducer 410 may be any arrangement that allows the specimen to be positioned such that the specimen will be exposed to a plasma sprayed by the ignition plug 300. For example, where the specimen is a solid, a support allowing relative positioning of the specimen and the ignition plug 300 would be acceptable. Where the specimen is a liquid, a flow tube, storage receptacle, or injector for the fluid would be acceptable. If the specimen is a fluid, a chromatography column or the like may be arranged further upstream from the specimen introducer 410.

The analyzer 411 may be selected appropriately according to the expected specimen. For example, one that carries out separation analysis of an excited specimen with an electric or magnetic field, such as a device employing magnetic field deflection, quadrupole, ion trap, time-of-flight, Fourier transform ion cyclotron resonance, or tandem technology, could be used. An optical analyzer composed of a photoreceiver, a spectroscope, and an optical system that ensures an optical path between the photoreceiver and spectroscope would be acceptable.

The detector 412 may be selected appropriately depending on the analysis technology of the analyzer 411. For example, electrons transported by an excited specimen could be multiplied and detected by an electron multiplier tube, microchannel plate detector, or the like. A Faraday cup or similar device for counting an excited specimen is also acceptable. A detector composed of a cloud chamber and an imaging device could also be used. If the analyzer 411 is an optical analyzer, the detector 412 may be a photodetector or image sensor employing an electron multiplier tube, a complementary metal oxide film semiconductor device, a charge-coupled device, or the like.

The signal processor 413 is specifically a computer (i.e., computer hardware, a program that runs on the computer hardware, and data provided to the computer). With regard to the signal processing method and method of presenting results to the user, ordinary known methods may be carried out appropriately depending, inter alia, on the class and model of the analyzer 411 and the detector 412 employed for the analysis. The operation of the computer is widely known, and thus a redundant description will not be provided here.

Although a specific form of embodiment of the instant invention has been described above and illustrated in the accompanying drawings in order to be more clearly understood, the above description is made by way of example and not as a limitation to the scope of the instant invention. It is contemplated that various modifications apparent to one of ordinary skill in the art could be made without departing from the scope of the invention which is to be determined by the following claims.

The invention claimed is:
1. An ignition plug comprising: a center electrode and a ground electrode for spark discharge;
   a center wire and an outside conductor forming a coaxial electromagnetic wave transmission line; and
   an electromagnetic radiation antenna that is electrically integrated with the center wire or the outside conductor;
   wherein the electromagnetic radiation antenna has a profile that defines part of a sphere or arc including a plurality of locations substantially equidistant from the center electrode.
2. The ignition plug according to claim 1 further comprising
   a dielectric member for covering the electromagnetic radiation antenna.
3. The ignition plug according to claim 2, wherein
   the dielectric member has a plurality of members having mutually different dielectric constants.
4. The ignition plug according to claim 1, wherein
   a basal part of the electromagnetic radiation antenna and an end of the outside conductor on the discharge gap side are embedded within the dielectric member.
5. The ignition plug according to claim 4, wherein
   a projecting portion that projects towards the discharge gap is disposed at an end on the discharge gap side of the dielectric member; and
   the electromagnetic radiation antenna curves along the surface of the projecting portion of the dielectric member.
6. The ignition plug according to claim 1, wherein
   the outside conductor is electrically integrated with the ground electrode, and forms a main fitting.
7. The ignition plug according to claim 1, wherein
   the insulating distance between the electromagnetic radiation antenna and the center electrode is greater than the insulating distance between the center electrode and the ground electrode; and the electromagnetic radiation antenna is situated to inward side of a thread when viewed from a discharge gap end.
8. A plasma generating equipment comprising:
   the ignition plug according to claim 1; and
   a cap having a conductor of substantially tubular shape open at both ends wherein one opening is closed, and the inside face in the vicinity of the other opening is disposed in contact with or in a threadably mated state with the main fitting of the ignition plug about the entire circumference;
   wherein the insulating distance between the cap and the center electrode of the ignition plug is shortest in the vicinity of the closed opening; and the volume of a space defined by the spark plug and the cap has been selected such that a rise in pressure in the space when a plasma is generated in the space will give rise to a pressure differential equal to or greater than a prescribed value between this space and a space communicating with this space via the opening.
9. The plasma generating equipment according to claim 8, wherein the cap becomes progressively thinner closer towards the opening.
10. The ignition plug according to claim 1, wherein the ground electrode, is integrated with the electromagnetic radiation antenna and constitutes a ring antenna.
11. The ignition plug according to claim 1 wherein the ground electrode, is integrated with the electromagnetic radiation antenna, and constitutes a coil antenna.
12. The ignition plug according to claim 1, wherein
    a stub is disposed in a basal part of the electromagnetic radiation antenna.
13. The ignition plug according to claim 1, further comprising:
    a vane wherein one end is joined to the antenna side end of the ground electrode, and the other end projects out towards the antenna.
14. The ignition plug according to claim 1, wherein
    the electromagnetic radiation antenna is branched at a minimum of one location.
15. An ignition plug comprising:
    a center electrode and a ground electrode for spark discharge;
    a center wire and an outside conductor forming a coaxial electromagnetic wave transmission line; and
    an electromagnetic radiation antenna that is capacitatively coupled to the center wire;
    wherein the ground electrode and the outside conductor are electrically integrated; and
    the electromagnetic radiation antenna is grounded by the outside conductor or the ground electrode, and has a profile that defines part of a sphere or arc including a plurality of locations substantially equidistant from the center electrode.
16. The ignition plug according to claim 15, wherein
    the ground electrode which has been integrated with the electromagnetic radiation antenna constitutes a ring antenna.
17. The ignition plug according to claim 15 wherein
    the ground electrode which has been integrated with the electromagnetic radiation antenna constitutes a coil antenna.
18. The ignition plug according to claim 15, wherein
    a stub is disposed in a basal part of the electromagnetic radiation antenna.
19. The ignition plug according to claim 15, further comprising:
    a vane wherein one end is joined to the antenna end of the ground conductor, and the other end projects out towards the antenna.
20. The ignition plug according to claim 15, wherein
    the electromagnetic radiation antenna is branched at a minimum of one location.

* * * * *